United States Patent [19]

Lee, Jr. et al.

[11] 4,340,532

[45] Jul. 20, 1982

[54] ADHESIVE COMPOSITIONS CONTAINING ALKOXY ALKYL ACRYLATES OR METHACRYLATES

[75] Inventors: Henry L. Lee, Jr., Pasadena; Giovanni Nolet, Westminster, both of Calif.

[73] Assignee: Lee Pharmaceuticals, Inc., South El Monte, Calif.

[21] Appl. No.: 139,360

[22] Filed: Apr. 11, 1980

[51] Int. Cl.$^3$ .................... C08K 3/40; C08F 220/20; A61K 5/06
[52] U.S. Cl. ................................ 524/854; 433/217; 433/224; 433/228; 526/313; 526/320; 523/219; 524/700
[58] Field of Search ............... 260/DIG. 36, 998.11, 260/42.52, 42.53, 42.29; 526/320, 313; 433/217, 228, 224

[56] References Cited

U.S. PATENT DOCUMENTS

| | | | |
|---|---|---|---|
| 3,697,490 | 10/1972 | Starmer | 526/281 |
| 3,784,540 | 1/1974 | Kliment et al. | 526/320 |
| 3,810,938 | 5/1974 | Schmitt et al. | 260/998.11 |
| 3,876,581 | 4/1975 | Neogi | 260/29.7 RP |
| 3,893,988 | 7/1975 | Seymour et al. | 526/320 |
| 3,923,740 | 12/1975 | Schmitt | 433/224 |
| 3,925,895 | 12/1975 | Kliment et al. | 433/224 |
| 4,028,295 | 6/1977 | Loshaek | 526/320 |
| 4,038,264 | 7/1977 | Rostoker et al. | 525/308 |
| 4,109,070 | 8/1978 | Loshaek et al. | 526/320 |
| 4,134,930 | 1/1979 | Kubota | 433/228 |
| 4,177,563 | 12/1979 | Schmitz-Josten et al. | 433/228 |
| 4,182,035 | 1/1980 | Yamauchi et al. | 260/998.11 |
| 4,228,265 | 10/1980 | Ohishi et al. | 526/320 |
| 4,256,603 | 3/1981 | Ibsen et al. | 260/998.11 |

FOREIGN PATENT DOCUMENTS

| | | | |
|---|---|---|---|
| 1446709 | 8/1976 | United Kingdom | 526/320 |
| 1483816 | 8/1977 | United Kingdom | . |
| 2010868 | 7/1979 | United Kingdom | 526/313 |
| 2034721 | 6/1980 | United Kingdom | 526/313 |

OTHER PUBLICATIONS

Chem. Abs. vol. 84-84823 (1974) Kimura et al., Japan 73-14655.
Chem. Abs. vol. 88 (1978) 90656n "Adhesives for Bending Metals" Tsuji et al.
Derwent Abs. 84044 y/47 "Fast Curing Adh. Comp.", TOA.60SE1 (Oct. 17, 1977).

*Primary Examiner*—Paul Lieberman
*Assistant Examiner*—Herbert J. Lilling
*Attorney, Agent, or Firm*—Irons and Sears

[57] ABSTRACT

Two component adhesive formulations are described that can be mixed to form compositions containing a curable liquid resin binder and filler. The liquid resin binder comprises from about 1% to about 60% of a lower alkoxy, lower alkyl methacrylate comprising methoxyethyl methacrylate, and from about 40% to about 99% of a polyunsaturated agent selected from the group consisting of aliphatic or aromatic diacrylates or dimethacrylates or mixtures thereof, the percentages being by weight based on the liquid resin binder. The filler forms up to 80% by weight of the adhesive composition and consists of finely divided inorganic filler, finely divided organic filler that may be soluble in the liquid resin binder, and mixtures thereof. The preferred compositions are useful as orthodontic adhesives and contain from about 10% to about 50% by weight of the liquid resin binder of methoxyethyl methacrylate.

25 Claims, No Drawings

ADHESIVE COMPOSITIONS CONTAINING ALKOXY ALKYL ACRYLATES OR METHACRYLATES

RELATED APPLICATION

Somewhat related subject matter appears in copending patent application Ser. No. 139,270, filed Apr. 11, 1980. The disclosure of this application is incorporated herein by reference.

BACKGROUND OF THE INVENTION

Orthodontic adhesive formulations utilized in the past for bonding stainless steel or plastic orthodontic brackets to tooth surfaces have generally been of the following types:

(1) a blend of an aromatic diacrylate with an aliphatic diacrylate, cured with a conventional catalyst-accelerator system;

(2) a blend of methyl methacrylate monomer with poly(methyl methacrylate) polymer using a peroxide or trialkyl borane curing catalyst;

(3) an aromatic diacrylate system containing a conventional ultraviolet-sensitive accelerator, cured with an ultraviolet ray gun, or, (4) a blend of an ester of methacrylic acid with a monoalcohol containing at least one epoxy group and finely divided filler material, in combination with a conventional catalyst-accelerator curing system.

The first three types of prior art adhesives are characterized by relatively poor water resistance, poor peel resistance, and poor retention to tooth enamel in orthodontic applications. These first three types of adhesive also are characterized by relatively poor adhesion to stainless steel (mesh) surfaces such as are found on stainless steel orthodontic brackets, and to polycarbonate plastics, of which orthodontic brackets are frequently made today. Adhesives in the fourth category are generally superior with respect to all of these characteristics, but may in some cases produce toxic reactions if contact is made with the skin.

Consequently, there is a need for new orthodontic adhesive formulations that possess the desired characteristics for such applications and that offer a choice of adhesive products to the dental profession and to the public.

There is also a need for adhesives for general purpose applications, where the adhesives are characterized by relatively high strength and fast setting times. Such adhesives are particularly useful in industrial applications involving the bonding of metals to plastics, and for bonding glass to the surfaces of other materials as in many electronic devices.

BRIEF SUMMARY OF THE INVENTION

This invention relates to adhesive compositions based on the use of methoxyethyl methacrylate together with a polyfunctional carboxylate cross-linking agent. More particularly, the invention relates to new orthodontic adhesive formulations based on the use of methoxyethyl methacrylate. This particular monomer material is not only a highly desirable monomer, but it also is an excellent solvent for other materials that are commonly used in formulations of this kind and, as well, it exerts a solubilizing effect upon polycarbonate articles with which the adhesives may be used, such as polycarbonate orthodontic brackets, thus permitting the development of a good bond.

These new adhesive compositions are intended to fill a need for adhesives that bond readily to several different types of materials. More particularly, there is a need for an orthodontic adhesive composition that provides good adhesion to polycarbonate plastic orthodontic brackets, to metallic orthodontic brackets, and to tooth enamel.

In addition to these necessary characteristics, an orthodontic adhesive formulation must be one that is completely acceptable in all respects for its intended use. That is, it must retain its strength in the oral cavity, despite the application of those normal stresses that occur in the oral cavity, and despite prolonged contact with fluids. In addition, the adhesive formulation in both its uncured and cured states must be physiologically acceptable and free from toxicity, so that it does not produce any untoward reactions.

The novel adhesive compositions of the present invention are based upon the use of a combination of methoxyethyl methacrylate with one or more modifying and/or cross-linking agents. The modifier or cross-linker may be for example, an aliphatic or aromatic diacrylate, an aliphatic or aromatic dimethacrylate, or mixtures of these.

For many applications, and particularly for orthodontic adhesives, the formulation may include a finely divided filler material that may be inorganic or organic. The filler may fulfill one or more important functions in the formulation: it tends to limit shrinkage upon curing; it also serves as a reinforcement; and it performs other functions recognized in the art, such as opacification, adjusting consistency, imparting lustre and/or sheen, providing color, etc. When an organic filler is used, generally it acts to increase the viscosity of the liquid present.

DETAILED DESCRIPTION OF THE INVENTION

Methoxyethyl methacrylate used alone in an adhesive composition as the curable monomer tends to produce soft and somewhat weak, gelatinous polymers.

Accordingly, in order to produce adhesive formulations from this monomer, to permit its use in adhesive formulations intended for high stress or structural applications, that is, applications analogous to orthodontic adhesive uses, cross-linking is necessary. When the cross-linking is provided, in accordance with the present invention, adhesives can be formulated having excellent mechanical properties and that are physiologically acceptable and of minimal or essentially no toxicity.

For adhesive compositions of general utility, very simple formulations can be prepared. These may comprise from a minor to a major amount by weight of the composition of methoxyethyl methacrylate, together with, as the balance of the active curable components, an aliphatic diacrylate or dimethacrylate, an aromatic diacrylate or dimethacrylate, or a mixture of any one or more of these. In addition, and optionally, other ethylenically unsaturated monomer materials may be present if desired. Other conventional adhesive components may also be present, particularly fillers, dyes, pigments, inhibitors, and a curing system such as the combination of a peroxide initiator (catalyst) and an accelerator.

These adhesive compositions are suitable for bonding a great many metals and plastics to a variety of substrates. They are suitable for numerous industrial applications in particular, where plastic-to-metal bonds are desirable, or where polycarbonate or other plastics, such as, for example, polyethylene, polypropylene, polytetrafluoroethylene, acrylic resins, and the like, must be bonded to one another. They are also suitable for such unusual applications, for example, as bonding polycarbonate horseshoes to horses' hooves. They are particularly desirable for use in the formulation of compositions for mending broken glassware and chinaware and the like. For such applications, a filler is selected with regard to its reflectance properties, and in this connection, finely divided magnesium oxide may well be selected for high reflectance compositions, whereas finely divided titanium dioxide would be selected for opaque compositions.

Other exemplary specific applications for the use of adhesive compositions in accordance with this invention are for bonding together the joints of irrigation pipes, assembling outdoor signs made of synthetic plastic materials, assembling components of metal to plastic or glass in electronic applications, bonding cable terminals and connecting wires, and other such uses where rapid setting times and high bond strengths may be desired.

A general purpose adhesive composition formulated in accordance with the present invention may have the following overall composition:

A. from about 1% to about 60%, and preferably from about 10% to about 50%, of methoxyethyl methacrylate (MEM), based on total monomer present;

B. based on total monomer present, from about 40% to about 99%, and preferably from about 50% to about 90%, of a modifier and/or cross-linking agent selected from the group consisting of aliphatic diacrylates and dimethacrylates, aromatic diacrylates and dimethacrylates, and mixtures thereof;

C. based on total adhesive composition, from about 0% to about 80%, preferably from about 20% to about 80%, and more preferably, 40% to 60%, of a finely divided filler selected from the group consisting of finely divided organic fillers and finely divided inorganic fillers and mixtures thereof that are insoluble in the adhesive composition;

D. a minor, effective amount of a conventional polymerization initiator (catalyst), preferably of the organic peroxide type, and E. a minor, effective amount of a conventional accelerator, preferably of the tertiary amine type.

The weight ratio of liquid resin binder to filler is selected so that the initial uncured mixture is either a flowable liquid or a workable paste. The preferred cross-linker monomers include mixtures of the aromatic dimethacrylates with polyalkylene glycol dimethacrylates.

For general adhesive purposes, a preferred selection of polymerizable components is a mixture of methoxyethyl methacrylate (MEM), ethoxylated bisphenol A dimethacrylate (EBA), and diethylene glycol dimethacrylate (DEGMA). Such a mixture will generate good general adhesive properties essentially in all proportions, but the proportions set out in Table 1 below are preferred, for the production of reasonable mechanical properties upon curing:

TABLE 1

| Formulation Ranges for General Adhesive Purposes | |
|---|---|
| Component | Percentages by Weight, Based upon Total Monomer Present |
| MEM | 1–60 |
| EBA | 20–70 |
| DEGMA | 0–60 |

For use with polycarbonate items, the content of MEM should be at least 30%, since MEM exerts a solubilizing effect on polycarbonate. It appears that the diethylene glycol dimethacrylate component, in this system, produces flexibility rather than the rigidity often associated with 3-dimensional structures produced by cross-linking. EBA is a thick material, and both of the other materials, especially MEM, serve as diluents with respect to EBA.

Unless adhesive compositions in accordance with the invention are being prepared for immediate use, two or more separate packages must be employed. Conveniently, one package may contain the monomer components and the accelerator, together with other minor ingredients, generally in liquid form, and a second package is used for a mixture of the filler component and catalyst, together with any other minor ingredients desired. Generally the filler component is in the form of a powder, so that often the adhesive will be packaged as a liquid component and a powder component. However, alternatives are available, such as two liquids, a liquid and a paste, or two pastes. Generally one of these packages contains an organic peroxide polymerization initiator (catalyst), and the other contains the accelerator, generally one of the tertiary amine type accelerators.

The formulation of orthodontic adhesive compositions is more demanding than the formulation of general purpose adhesives. Accordingly, rather specific formulation proportions have been found to be desirable for these compositions. The proportions of liquid resin binder relative to filler are generally selected so that the uncured adhesive composition after mixing is either a viscous liquid or a workable paste. Thus, orthodontic adhesive compositions are preferably formulated from:

A. based upon total monomer present, about 10% to 50%, and preferably, from about 30% to about 50%, of methoxyethyl methacrylate;

B. based upon total monomer present, from about 50% to about 90%, and preferably from about 50% to about 70%, of a modifier or cross-linking agent, or combination thereof, selected from the group consisting of aliphatic dimethacrylates, aromatic dimethacrylates and mixtures thereof;

C. based on total adhesive composition, from 0% to about 80%, and preferably from about 20% to about 80%, and most preferably from about 40% to about 60%, of a finely divided filler that may be organic or inorganic or a mixture of these, and which is generally insoluble in the adhesive under the conditions of use to which the adhesive will be subjected;

D. based on total adhesive composition, less than about 5% of a conventional polymerization initiator (catalyst), preferably of the organic peroxide type, preferably benzoyl peroxide (BPO); and E. a minor amount of a conventional accelerator, preferably of the tertiary amine type.

The preferred cross-linker is a mixture of an aliphatic dimethacrylate and an aromatic dimethacrylate.

For orthodontic adhesives, a preferred selection of polymerizable components is a mixture similar to that described above for general adhesive purposes. The proportions are more carefully defined, however, to produce desirable physical properties for this demanding use:

TABLE 2

Orthodontic Adhesives
Percentages by Weight of Preferred Components
Based on Total Monomer

|  | Useful | Preferred | Very Preferred |
|---|---|---|---|
| MEM | 1–60 | 10–50 | 50 |
| EBA | 20–70 | 25–55 | 30 |
| DEGMA | 0–60 | 5–60 | 20 |

Again, for use with polycarbonate brackets, an MEM content of at least 30% is needed, for good adhesion.

The filler for an orthodontic adhesive formulation is an optional ingredient. It may be any finely divided inorganic filler material that would be suitable for use in the oral cavity. When an inorganic filler is emloyed, it is preferably treated before use with a keying agent, such as a silane, to improve the bond between the filler and the resinous environment surrounding it. Similarly, any organic filler may be employed that is suitable for use in the oral cavity. Preferred fillers are very finely divided particulate polymeric filler materials, that is, those having average apparent diameters in the range from about 0.04 micrometers to about 0.07 micrometers.

A very preferred filler material is poly(methyl methacrylate). Thus a very preferred orthodontic adhesive composition would include the very preferred monomer selection and proportions shown in Table 2 to 100 total parts of monomer, together with about 10 parts of polymethyl methacrylate in the liquid portion, and in the powder portion, about 58 parts of polymethyl methacrylate, about 42 parts of silica, and other usual minor components.

If these proportions are calculated, then a very preferred composition for orthodontic applications can be described as follows:

TABLE 3

Orthodontic Adhesive

| Ingredient | Percentage by Weight Based on the Sum of these Ingredients |
|---|---|
| MEM | 23.8 |
| Cross-linkers | 23.8 |
| Fillers | 52.4 |

An alternative very preferred powder portion has the approximate composition of 58–60 parts of polymethyl methacrylate, 40–42 parts of barium silicate, and based on total poweder weight, about 1% BPO and about 2% $TiO_2$ as an opaquing agent. In these preferred adhesive compositions, the filler components provides about 50% to about 54% of the total composition.

In preparing orthodontic adhesive formulations, all of the components should be selected so that the formulation is nonallergenic as well as nontoxic. On the basis of dermatological testing performed on a number of persons, and other tests, the compositions herein contemplated have acceptable properties.

The inorganic fillers, such as finely divided alumina, silicates, silica, quartz, glass, and the like, are used to control consistency of the material and to improve its physical and mechanical properties.

Generally, a polymeric filler material which is partially soluble or insoluble is present. Suitable for and very effective in the compositions of the present invention are copolymers of ethyl and methyl methacrylate; polymethyl acrylate; polyethyl acrylate, and polypropyl acrylate.

A wide variety of modifiers and cross-linking agents may be employed, and these are generally well recognized in the art. One preferred modifying and cross-linking agent is a mixture of diethylene glycol dimethacrylate and ethoxylated bisphenol A dimethacrylate, in the proportions mentioned above. However, many other diacrylates and dimethacrylates may be employed, such as, for example, the polyalkylene glycol dimethacrylates in general, and 4,4-diphenylene dimethylacrylate, as well as other aromatic dimethacrylates.

Among the crosslinking monomers herein contemplated are 2,2 bis[4'-(3''-methacryloyl-2''-hydroxypropoxy)phenyl] propane; mono-, di-, tri-, tetra-, and polyethylene glycol dimethacrylates; diallyl fumarate; 2,2 bis (4'-methacryloyl phenyl) propane; 2,2 bis(4'-methacryloylethyloxyphenyl) propane; diallylphthalate; bis(2-methacryloylethyl) o-, m-, and p-phthalates, and 2-acryloylethylmethacrylate.

Other similar crosslinking monomers having at least two groups or moieties, such as allyl, acryloyl, methacryloyl or other similar unsaturations, capable of polymerizing in the presence of the initiators and accelerators used in the present invention are herein contemplated. Typically, these monomers are not only mono-polymerizable, and copolymerizable, but they are suitable crosslinking agents for acrylic polymers.

Typical diluent monoacrylates (particularly acrylic and methacrylic esters) within the purview of the present invention are substituted, lower alkyl or hydroxyalkyl ($C_1$-$C_5$) and cycloalkyl methacrylates, including but not limited to methyl methacrylate, hydroxyethyl methacrylate, cyclohexyl methacrylate and cyclopentyl methacrylate, and tetrahydrofurfuryl methacrylate. Obviously, substituent moieties other than hydroxy which do not interfere with or significantly disrupt the intended polymerization reaction are herein contemplated.

Of the initiators herein contemplated, the preferred are the free radical catalysts, such as the organic peroxides and particularly benzoyl peroxide and lauroyl peroxide.

Useful accelerators are the tertiary amines, especially N,N-di(lower)alkyl-p-toluidines (e.g., N,N-dimethyl-p-toluidine, N,N-diethyl-p-toluidine), the N,N-bis(lower hydroxyalkyl) p-toluidines, and N,N-di(lower)alkyl anilines, such as N,N-dimethyl aniline.

Of course, other conventional free radical catalysts and promoters, while not at present preferred, may be used in lieu of or in conjunction with (when compatible) the foregoing.

The set time for the adhesive compositions of the present invention, usually up to about 600 or so seconds, and generally adjusted to be 120 to 600 seconds, may be regulated by varying the concentration of initiators and/or accelerators. Faster set times than 120 are readily attainable by adjusting the catalyst-accelerator system. Representative concentrations of benzoyl peroxide are in the range from 0.2% to about 4% based on total monomer, and for N,N-dimethyl-p-toluidine, about 0.1% to about 8.0%, also based on total monomer present.

Minor conventional amounts of modifiers may also be present, such as dyes, opaquing agents (e.g., titanium dioxide), and stabilizers (e.g., 3-butyl-4-hydroxytoluene).

The ratio of the one component to the other may vary from about 3:1 to about 1:3, depending upon the application properties desired, so long as the component concentrations in the resulting mixture are within the range herein recited. The 3:1 to 1:3 combinations can be formulated to mix well and to flow well, and to cure reliably with reproducible set times and superior and reproducible physical and mechanical properties. For simplicity, however, an essentially 1:1 ratio is preferred and is most easily practiced.

The invention will now be further demonstrated by reference to several specific examples thereof. Throughout this application and particularly in the examples, all references to parts and percentages are by weight unless expressly stated to be otherwise. All temperatures are in degrees Celsius.

EXAMPLE 1

Orthodontic Adhesive Formulation

The following ingredients were employed to make the liquid component:

| Material | Parts by Weight |
|---|---|
| Liquid Component | |
| methoxyethyl methacrylate | 5 |
| diethylene glycol dimethacrylate | 2 |
| ethoxylated bisphenol A dimethacrylate | 3 |
| 3-tertiary-butyl-4-hydroxytoluene | 0.006 |
| Spectrasorb U.V. inhibitor | 0.050 |
| poly(methyl methacrylate) powder | 1.000 |
| N,N-bis (2-hydroxyethyl) p-toluidine | 0.18 |
| Powder Component | |
| copolymer, polyethyl and polymethyl methacrylates, impregnated with about 2.5% by weight benzoyl peroxide | 5.88 |
| titanium dioxide | 0.044 |
| amorphous silica | 4.12 |
| solution of 3-methacryloxy propyl trihydroxy silane at about 2.6% concentration in methylene chloride (for application to the silica) | 1.88 |

After treatment of the silica with the silane solution, and drying, the liquid and powder components were mixed together in a 1:1 ratio by weight, to form an adhesive composition. The composition cured rapidly at room temperature. As cured, it was subjected to several tests. The results reported below are based on averaged values from several specimens.

Rockwell hardness upon curing was about 110, and after storage in a water bath for 5 weeks, an average value of about 109 was observed.

An orthodontic adhesion test, in which the adhesive is applied between a plastic bracket and bovine tooth enamel, produced an average adhesion failure value of about 19.4 lbs. after 1 day of storage in a water bath, failure generally being at the tooth surface. After six weeks in the water bath, the value was about 14.7 lbs., failure being at the tooth. A similar test with a metal bracket produced an average adhesion test value of about 20.5 lbs., failure sometimes occurring at the bracket and at other times, at the tooth surface. After storage for 1 day in water, the value was about 21.1 lbs., failure being generally at the bracket surface. After 4 weeks of storage in a water bath, the average diametral tensile strength observed was about 3259 psi.

The liquid component remained stable after storage of samples for 27 days at room temperature, at 37° C., and in a refrigerator respectively.

EXAMPLE 2

Modified Orthodontic Adhesive Formulation

An adhesive was prepared for use by admixture of the following:

| Material | Parts by Weight |
|---|---|
| Liquid Component | |
| methoxyethyl methacrylate | 5 |
| ethoxylated bisphenol A dimethacrylate | 1 |
| diethylene glycol dimethacrylate | 4 |
| 3-t-butyl-4-hydroxytoluene | 0.006 |
| Spectrasorb U.V. inhibitor | 0.15 |
| polymethyl methacrylate powder | 0.7 |
| N,N-bis(2-hydroxyethyl)p-toluidine | 0.15 |
| Powder Component | |
| copolymer of methyl methacrylate and ethyl methacrylate in a 70/30 weight ratio, impregnated with 2.6% by weight of benzoyl peroxide | 60 |
| polymethyl methacrylate powder | 40 |
| titanium dioxide | 0.1 |

The liquid and powder components were mixed together in an approximately 1:1 ratio by weight, to form a curable adhesive composition. The composition sets rather rapidly at room temperature and must be used promptly after mixing the two components. This adhesive formulation was subjected to several tests.

An adhesion test was made in which the adhesive was employed to secure a metal orthodontic bracket to bovine enamel. After storage for one day in a water bath maintained at 37° C., the samples withstood an average force of about 20 lbs., before failing. Failure generally was at the bracket.

The adhesive was also evaluated in tests in which a plastic bracket was secured to bovine enamel. After storage for one day in a water bath at room temperature, the adhesive withstood a force of about 20 lbs. Failure generally occured at the bracket.

Generally favorable results were observed with staining tests, Rockwell hardness tests, diametral tensile strength, and immediate and deferred adhesion tests with both plastic and metal brackets.

Set time for the adhesive was generally less than two minutes at room temperature (24° C.), and remained essentially constant even after storage at 37° C. over a period of time.

EXAMPLE 3

General Purpose Adhesive Composition

The following ingredients were formulated as liquid components of two-package adhesive formulations:

| | Liquid Component | | | |
|---|---|---|---|---|
| | Parts by Weight | | | |
| Material | 3-1 | 3-2 | 3-3 | 3-4 |
| methoxyethyl methacrylate | 20 | 10 | 8 | 5 |
| N,N-bis (2-hydroxyethyl) p-toluidine | 0.5 | 0.25 | 0.25 | 0.25 |
| 3-t-butyl-4-hydroxytoluene | 0.12 | — | 0.006 | — |
| poly(methyl methacrylate) | 1.4 | 1.4 | 0.7 | 0.7 |
| polyethylene glycol | | | | |

-continued

| | Liquid Component | | | |
|---|---|---|---|---|
| | Parts by Weight | | | |
| Material | 3-1 | 3-2 | 3-3 | 3-4 |
| dimethacrylate | — | — | 2 | 5 |

These were used with the powder component of Ex. 2, in each case in an approximately 1-to-1 weight ratio. Observed set times after mixing, in seconds, were:

| 3-1 | 3-2 | 3-3 | 3-4 |
|---|---|---|---|
| 500 | 360 | 200 | 130 |

The average adhesion test values, using these adhesives to bond plastic orthodontic brackets to bovine tooth enamel, after 24 hours in a water bath at 37° C., were:

| | 3-1 | 3-2 | 3-3 | 3-4 |
|---|---|---|---|---|
| Avg. adhesion in lbs. | 10.4 | 15.2 | 9.4 | 8.0 |

All of these were useful as rapid setting general purpose adhesives, with good bonding ability to a variety of surfaces.

EXAMPLE 4

Modified General Purpose Adhesive Formulation

The following liquid component was prepared:

| Material | Parts by Weight |
|---|---|
| methoxyethyl methacrylate | 5 |
| diethylene glycol dimethacrylate | 5 |
| N,N-bis(2-hydroxyethyl)p-toluidine | 0.25 |
| polymethyl methacrylate powder | 0.7 |
| 3-t-butyl-4-hydroxytoluene | 0.006 |

This liquid component was mixed, for use, with the same powder component as in Ex. 2, in an approximately 1-to-1 weight ratio.

Set time was about 110 seconds. This preparation bonded well to tooth surfaces, but also is a good general purpose, rapid setting adhesive. It exhibited a relatively lower adhesion of metal mesh and of plastic to bovine tooth enamel, but had high adhesion of polycarbonate surface to polycarbonate surface.

EXAMPLE 5

Variations in the Formulation of the Liquid Component

Eighteen different liquid compositions were prepared, to permit a comparison of adhesion values. The several compositions are described below in Table 4.

TABLE 4

| Ingredient | 5-1 | 5-2 | 5-3 | 5-4 | 5-5 | 5-6 | 5-7 | 5-8 | 5-9 | 5-10 | 5-11 | 5-12 | 5-13 | 5-14 | 5-15 | 5-16 | 5-17 | 5-18 |
|---|---|---|---|---|---|---|---|---|---|---|---|---|---|---|---|---|---|---|
| methoxyethyl methacrylate | 3 | 4 | 2 | 5 | 6 | 7 | 2 | 2 | 1 | 1 | 5 | 3 | 7.5 | — | 5 | 10 | — | — |
| diethylene glycol methacrylate | 4 | 2 | 3 | 1 | 2 | 1 | 2 | 6 | 4.5 | 2 | 4 | 1 | 1.5 | 5 | — | — | 10 | — |
| ethyloxylated bisphenol A dimethacrylate | 3 | 4 | 5 | 4 | 2 | 2 | 6 | 2 | 4.5 | 7 | 1 | 6 | 1.0 | 5 | 5 | — | — | 10 |
| t-butyl hydroxy toluene | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 |
| 2-hydroxy methoxy benzophenone | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| polymethyl methacrylate powder | 0.8 | 0.6 | 0.6 | 0.72 | 0.83 | 0.95 | 0.7 | 0.95 | 0.7 | 0.6 | 1.5 | 0.7 | 1.5 | 0.65 | 0.65 | 0.8 | 0.8 | — |
| N,N-bis (2 hydroxyethyl) p-toluidine | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 |

In an evaluation of each of these liquid components, each was mixed in an approximately 1:1 weight ratio with the powder component of Ex. 1. The properties were then observed when each adhesive preparation was employed to bond a plastic orthodontic bracket to bovine tooth enamel, after one day of storage in a water bath at 37° C. The results are tabulated below in Table 5.

TABLE 5

| Adhesive Prepared from a 1:1 Mixture of the Ex. 1 Powder and Liquid Component Formulation No. | Adhesion Values After 1 day in a water bath at 37° C. | | Adhesion Values After 2 weeks in a water bath at 37° C. | |
|---|---|---|---|---|
| | Highest Value (in lbs) | Average Value (in lbs) | High Value (in lbs.) | Average Value (in lbs.) |
| 5-1 | 17.5 | 13.1 | 19.5 | 15.41 |
| 5-2 | 22.0 | 17.7 | 25.5 | 19.0 |
| 5-3 | 14.6 | 10 | 19.5 | 15.5 |
| 5-4 | 14 | 8.8 | 14.0 | 11.9 |
| 5-5 | 11.6 | 9.7 | 17.2 | 9.3 |
| 5-6 | 12.2 | 9.3 | 8.4 | 6.6 |
| 5-7 | 24.0 | 19.5 | 12.0 | 9.9 |
| 5-8 | 16.4 | 13.4 | 22.5 | 15.0 |
| 5-9 | 19.8 | 18.1 | 18.6 | 17.1 |
| 5-10 | 23.5 | 17.6 | 16.0 | 11.3 |
| 5-11 | 9.0 | 6.4 | 7.65 | 6.8 |
| 5-12 | 16.2 | 13.1 | 25.0 | 18.4 |
| 5-13 | 11.0 | 7.6 | 10.6 | 7.9 |
| 5-14 | 23.0 | 20.6 | 29.5 | 22.7 |
| 5-15 | 17.4 | 15.4 | 23.0 | 20.5 |
| 5-16 | 12.2* | 8.5* | — | — |
| 5-17 | 14.2* | 10.7* | — | — |
| 5-18 | very weak** | | — | — |

*after 6 hours in a water bath at 37° C.
**the brackets were released in handling.

EXAMPLE 6

Variations in the Formulation of the Powder Component

Several different powder component formulations were prepared to permit comparisons, as described in Table 6 below:

TABLE 6

| Materials | Powder Component Formulations Parts by Weight, Formulation No. | | | | | | |
|---|---|---|---|---|---|---|---|
| | 6-1 | 6-2 | 6-3 | 6-4 | 6-5 | 6-6 | 6-7 |
| copolymer, ethyl and methyl methacrylates impregnated with about 2.6% by weight benzoyl peroxide | 40 | 40 | 40 | 40 | 40 | 40 | 58 |
| powdered polymethyl methacrylate, impregnated with about 2/5% by weight benzoyl peroxide | 57 | 57 | 57 | 56 | 56 | 56 | — |
| $TiO_2$ | 3.0 | 2.0 | 1.5 | 1.0 | 2.5 | 2.0 | 0.2 |
| Fine Silica | 0.1 | — | — | 3.0 | 1.5 | 2.0 | 42 |

These powder formulations were made into adhesive compositions by approximately 1:1 admixture with the liquid component of Ex. 1. The adhesion values generally averaged well above 15 lbs.

EXAMPLE 7

Orthodontic Adhesive Formulation; Different Combinations

The liquid component of Example 1 was combined, 1:1, with the powder component of Ex. 2, to make an adhesive preparation. It was evaluated by adhesion of plastic brackets to bovine tooth enamel. After storage at 37° C. for one day in a water bath, the average adhesion value at break was 18.9 lbs. The results of a compressive strength test indicate that the adhesive preparation is plastic. The material did not break under compressive stress, but the length was reduced. Diametral tensile strength test results averaged out at about 3,483 psi, on samples tested after 3 days storage at 37° C. in a water bath.

EXAMPLE 8

White Orthodontic Adhesive Powder Formulations and Adhesives Made From Them

The following powder formulations are white and do not discolor in use:

TABLE 7

| Materials | Powder Component Formulations Parts by Weight, Formulation No. | | | |
|---|---|---|---|---|
| | 8-1 | 8-2 | 8-3 | 8-4 |
| copolymer, ethyl and methyl methacrylates, impregnated with about 2.6% by weight BPO | 5.88 | 5.88 | 5.88 | — |
| | — | — | — | 5.73 |
| titanium dioxide | 0.022 | 0.022 | 0.022 | 0.022 |
| barium glass beads impregnated with BPO*, and wetted with $CH_2Cl_2$ | 4.12 | 4.09 | 4.08 | 4.27 |
| *% by wt. BPO based on barium glass beads plus BPO | 4.5% | 3.4% | 2.3% | 5.5% |
| set time after mixing approx. 1:1 with the liquid component of Ex. 1, seconds | 75 at 24.3° C. | 80 at 24.6° C. | 92 at 26.6° C. | 92 at 26.6° C. |

The adhesive composition prepared by mixing the 8-3 powder with the liquid component of Ex. 1, approximately 1:1, was evaluated for adhesion of metal brackets to bovine tooth enamel. After storage in a water bath at 37° C. for one day, the average adhesion value at break was 20.7 lbs.

The barium glass beads used are commercially available for use in dental restorative composites. Their use leads to a white adhesive that does not discolor. They may be used as is or combined with other inorganic fillers such as silica, and also with polymeric fillers, or with combinations of such materials.

GENERAL

In the foregoing examples of the invention, the alkoxy alkyl methacrylate employed has been used in combination with a second, di-ethylenically unsaturated monomer material. The use of such a modifier and/or cross-linker is highly desirable, in order to achieve rapid setting times, higher structural strength, and to modify the softness of methoxyethyl methacrylate upon polymerization.

Typically the amount of cross-linker has been 50% or more, and the amount of the monoethylenically unsaturated monomer has been indicated to be in the range from about 1% to about 60%. For general adhesive purposes, particularly where the liquid portion contains relatively large amounts of dissolved polymeric filler, somewhat higher amounts of the monoethylenically unsaturated monomer than 50% may be used, particularly where the formulation is done in such a way as to balance the properties.

The preferred curable monofunctional monomer is methoxyethyl methacrylate. It has good etching power for polycarbonate brackets. It is also a solvent for polymethyl methacrylate, so that that polymer, when used in the liquid portion, acts as a thickener rather than as a filler. Only the monofunctional monomers have etching power for polycarbonate plastics. However, generally, the greater the etching power, the greater the propensity to act as an irritant to tissue. In this respect methoxyethyl methacrylate is very valuable, since it is a good etchant but is not an irritant. For this reason it is preferably used as the only monofunctional monomer in orthodontic adhesive formulations. The difunctional cross-linking monomers are employed to impart strength and other characteristics to adhesive formulations.

Several other monofunctional monomers have etching power for polycarbonates and thus are useful either as diluents in minor amounts, or as comonomers in any proportion desired in general purpose adhesive formulations, especially those intended for use with polycarbonate plastics. Such monomers include, in order of observed decreasing ability to etch polycarbonate: methyl methacrylate, glycidyl methacrylate, methoxy ethoxy ethyl methacrylate, benzoyl methacrylate, acetol methacrylate

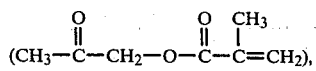

methyl glycolate methacrylate, and butyl methacrylate. Other monomers that can be used as diluents, but that have little etching power for polycarbonates, include phenyl methacrylate, trichloroethane methacrylate, 1,3-dichloro-2-propyl methacrylate, p-cresyl methacrylate, crotyl methacrylate, and tetrahydrofurfuryl methacrylate.

CONCLUSION

While the invention has been disclosed herein by reference to the details of preferred embodiments thereof, it is to be understood that such disclosure is intended in an illustrative rather than in a limiting sense, and it is contemplated that various modifications in the compositions of the invention will readily occur to those skilled in the art, within the spirit of the invention and the scope of the appended claims.

What is claimed is:

1. In an adhesive composition comprising a curable liquid resin binder and effective amounts of polymerization initiator and accelerator, respectively, the improvement comprising:
   a curable liquid resin binder comprising, in percentage by weight based on the resin binder:
   from about 1% to about 60% of (A) a lower alkoxy alkyl methacrylate comprising methoxyethyl methacrylate, and
   from about 40% to about 99% of (B) a polyunsaturated, copolymerizable agent selected from the group consisting of aliphatic diacrylates and dimethacrylates, aromatic diacrylates and dimethacrylates, and mixtures thereof, and
   from 0% to about 80% of the total adhesive composition of a finely divided filler selected from the group consisting of finely divided inorganic fillers, finely divided organic fillers, and mixtures thereof.

2. The adhesive composition of claim 1 wherein the (A) component is present in the binder in an amount from 10% to about 50% by weight thereof, and the (B) component is present in an amount from about 50% to about 90% by weight thereof.

3. The adhesive composition of claim 2 wherein said filler component is present in an amount from about 20% to about 80% by weight.

4. The adhesive composition of claim 1, 2, or 3, wherein the agent (B) is a mixture of a poly(alkylene glycol) dimethacrylate with an aromatic dimethacrylate.

5. The adhesive composition of claim 1, 2, or 3, wherein the agent (B) is a mixture of aliphatic and aromatic dimethacrylates.

6. The adhesive composition of claim 1 wherein the (A) component is present in the binder in an amount from 10% to 50% by weight thereof, the (B) component is present in an amount from about 50% to about 90% by weight thereo, and said filler component is present in an amount from about 40% to 60% by weight of the composition.

7. The adhesive composition of claim 1, 2, or 6, wherein the curable liquid resin binder comprises at least 30% by weight of methoxyethyl methacrylate, by weight of the binder.

8. An adhesive composition having a curable liquid resin binder and containing effective amounts of polymerization initiator and accelerator respectively, exhibiting practical bond strength toward at least stainless steel mesh, polycarbonate plastics, and tooth enamel, consisting essentially of:
   from about 30% to about 50% by weight of the binder of (A) methoxyethyl methacrylate, and
   from about 50% to about 70% by weight, based on the liquid resin binder, of (B) a polyunsaturated, copolymerizable agent selected from the group consisting of aliphatic dimethacrylates, aromatic dimethacrylates, and mixtures thereof; and
   from 0% to about 80%, based on the total composition, of a finely divided filler selected from the group consisting of finely divided organic fillers, finely divided inorganic fillers, and mixtures thereof.

9. The adhesive composition of claim 8 wherein said filler component comprises from 20% to 90% by weight of the adhesive composition.

10. The adhesive composition of claim 9 wherein said filler component comprises from 40% to 60% by weight of the adhesive composition.

11. An orthodontic adhesive formulation made up of a mixture of a liquid resin binder, filler, and effective amounts of an organic peroxide initiator and a tertiaryamine accelerator, the amounts being effective to cause polymerization to occur within up to about 600 seconds after mixing of the components, said liquid resin binder consisting essentially of:
    from about 10% to about 50% by weight of the binder of methoxyethyl methacrylate, and
    from about 50% to about 90% by weight of the binder of a polyunsaturated copolymerizable agent selected from the group consisting of aliphatic dimethacrylates, aromatic dimethacrylates, and mixtures thereof, and
    from about 20% to about 80% by weight of the adhesive composition of a finely divided filler selected from the group consisting of finely divided organic fillers, finely divided inorganic fillers, and mixtures thereof;
    the adhesive being formulated so that the initial mixture, in its uncured state, is either a viscous liquid or a workable paste.

12. The adhesive of claim 11 wherein the polyunsaturated agent is a mixture of exthoxylated bisphenol A dimethacrylate and diethylene glycol dimethacrylate.

13. The adhesive formulation of claim 12, wherein the binder consists of methoxyethyl methacrylate, 30% to 50%, and polyunsaturated agent, 50% to 70%.

14. The adhesive formulation of claim 13 wherein the polyunsaturated agent consists of a mixture of, in percentages by weight based on the binder, 25% to 55% of ethoxylated bisphenol A dimethacrylate and 5% to 60% of diethylene glycol dimethacrylate.

15. The adhesive of claim 13 wherein the filler component comprises from 40% to 60% by weight of the composition.

16. The adhesive of claim 13 wherein the filler comprises barium glass beads.

17. The adhesive of claim 15 wherein the filler consists of a mixture of organic polymeric and inorganic filler particles.

18. The adhesive of claim 17 wherein the inorganic filler particles comprise barium glass.

19. The method of utilizing an adhesive in accordance with claim 11, to bond an article having a metal mesh surface or a synthetic plastic surface to tooth enamel comprising applying said adhesive to the surface of said article or said enamel surface or both and joining the two surfaces to form a bond.

20. An adhesive bond cured from a composition according to claim 1, 8, 11, 13, or 14.

21. A curable composition comprising, as the polymerizable portion thereof, a mixture in percentages by weight of: a lower alkoxy lower alkyl methacrylate monofunctional monomer comprising methoxyethyl methacrylate, from 1% up to about 60%; ethoxylated bisphenol A dimethacrylate, 20% to 70%, and diethylene glycol dimethacrylate, from 0% to 60%.

22. The composition of claim 21 wherein the amounts are about:

| | |
|---|---|
| monofunctional monomer ethoxylated bisphenol A dimethacrylate | 10% to 50% |
| diethylene glycol dimethacrylate | 25% to 55% |
| | 5% to 60% |

23. The composition of claim 22 wherein the amount of methoxyethyl methacrylate present is at least 30%.

24. The composition of claim 21 wherein the amounts are about:

| | |
|---|---|
| monofunctional monomer | 50% |
| ethoxylated bisphenol A dimethacrylate | 30% |
| diethylene glycol dimethacrylate | 20% |

25. The composition of claim 24 wherein the monofunctional monomer consists essentially of methoxyethyl methacrylate.

* * * * *